US00PP24181P3

(12) United States Plant Patent
Aughenbaugh

(10) Patent No.: US PP24,181 P3
(45) Date of Patent: Jan. 21, 2014

(54) HYBRID TOMATO PLANT NAMED 'ESAS'

(50) Latin Name: ***Solanum lycopersicum×Capsicum anuum* 'Esas'**
Varietal Denomination: Esas

(76) Inventor: Ernest S. Aughenbaugh, St. Johns, MI (US)

( * ) Notice: Subject to any disclaimer, the term of this patent is extended or adjusted under 35 U.S.C. 154(b) by 159 days.

(21) Appl. No.: 12/932,523

(22) Filed: Feb. 28, 2011

(65) Prior Publication Data

US 2012/0222182 P1 Aug. 30, 2012

(51) Int. Cl.
*A01H 5/00* (2006.01)

(52) U.S. Cl.
USPC ..... Plt./261; Plt./258

(58) Field of Classification Search
USPC ..... Plt./261, 258, 263.1; 800/317, 317.1, 800/317.4
See application file for complete search history.

(56) References Cited

U.S. PATENT DOCUMENTS

| | | | | |
|---|---|---|---|---|
| PP4,539 | P | 5/1980 | Briggs | |
| PP5,171 | P | 1/1984 | Briggs | |
| PP5,812 | P | 11/1986 | Pezzulla | |
| 6,140,561 | A * | 10/2000 | Yonemaru et al. | 800/317 |

OTHER PUBLICATIONS

Rutgers New Jersey Agricultural Experimental Station 2012, Burgess Stuffing Tomato, retrieved on Oct. 1, 2012. Retrieved from the Internet at <http://njaes.rutgers.edu/tomato-varieties/variety.asp?Burgess+Stuffing+Tomato> one page.*

Trademark Electronic Search System. Tulip Tomato, retrieved on Oct. 16, 2012. Retrieved from the Internet at <http://tess2.uspto.gov/bin/showfield?f=doc&state=4003:tmd7gk.2.21> 2pp.*

Savonen. Save your favorite non-hybrid tomato seeds for next year. Oregon State University Extension, 2006, retrieved on Apr. 3, 2013. Retrieved from the Internet at <http://extension.oregonstate.edu/gardening/node/609/print> 2 pp.*

* cited by examiner

*Primary Examiner* — June Hwu
(74) *Attorney, Agent, or Firm* — Technology Law, PLLC; Karen L. Kimble

(57) ABSTRACT

A new and distinct variety of paste-type hybrid tomato plant (*Solanum lycopersicum×Capsicum anuum* 'Esas') is described that is believed derived in part from an Amish tomato, and in part from a Big Bertha Pepper. This hybrid tomato 'Esas' has 2-4 lobes similar to a pepper, a hardy skin, and remains on the vine when ripe until frost. When picked ripe, this tomato lasts longer without rotting than normal tomatoes. Some of these tomatoes have been eaten after 1 to 8 months from picking. The fruit usually shrinks inside itself after some time from picking.

6 Drawing Sheets

Latin name of the genus and species of the plant claimed: *Solanum lycopersicum×Capsicum anuum* 'Esas'.

Variety denomination: "ESAS".

BACKGROUND OF THE INVENTION

The present plant is a new and distinct hybrid tomato plant which was a selection taken from plants found in a cultivated area and then asexually and/or sexually reproduced. The cultivated area was Applicant's garden of about 40 feet by 80 feet where tomatoes, peppers, onions, squash, beans, peas, beets, kohlrabi, turnips and other vegetables as desired are grown in a season. The year when this hybrid was found, Applicant was growing Big Bertha peppers (*Capsicum anuum*) as the only pepper in his garden; the next row had Amish tomatoes (*Solanum lycopersicum*); then other rows farther removed from the hybrid plant had Big Boy, Better Boy, Beefsteak and Yellow Girl tomatoes growing. To Applicant's best knowledge and belief, the cross was made by a bee. The new hybrid was found in one of the rows of Amish tomatoes where the plant was not tilled under.

Seeds were grown out from the first plant for sexual reproducing the plant and cuttings of the plant done for asexually reproducing the plant where the plant part (e.g. the stem) was directly planted into the soil without any pretreatment or root growth hormone added. The plant stem formed roots and produced fruit as did the seeds. Selection of subsequently growing plants was based on the shape of the fruit and the hardy skin. Selected seed and/or cuttings were again grown out and planted near Amish tomato plants. Selection was again made using the same criteria. This was repeated three times. Selection from the last named generation was based on shape, hearty skin, and ability to remain on the vine after ripened. Surprisingly, the hybrid plant has grown to type and is stable for its traits as discussed herein for the last nine years. No further crosses of the parents have been made. Other characteristics of the hybrid plant are stated below.

Asexual reproduction of the new hybrid tomato plant by cuttings in my garden in St. Johns, Mich.

DESCRIPTION OF PARENTS

Amish tomato, the seed parent, can be both indeterminate and determinate; this parent plant was indeterminate, and is a member of the Roma family. They are disease resistant to fusarium wilt and verticillum. The Amish tomato is a medium size fruit and a usual shape for the Roma family with a rounded or pointed end. The usual Amish tomato believed to be the parent variety is shown in some of the photographs provided with this application.

Big Bertha Pepper, the pollen parent, is a green pepper and has no use as a tomato. As with most peppers, this tomato has characteristics of definite lobes, internal ridges, and retention on the plant on the vine after ripened.

In contrast to the present hybrid, Burgess Stuffing tomatoes are hollow inside with seeds resting at the top of the tomato, similar to a pepper. They have 3 lobes and their size is larger than the present hybrid tomato. The present hybrid tomatoes have seeds all through their cavities, in a manner more like a tomato (see FIG. 6). Toma-P had no picture in U.S. Pat. No. 6,140,561 but states it is a hybrid by cross-breeding of Mexican, Indian, Hungarian, Dutch and Canadian paprika, Japanese tomatoes and Japanese peppers; and it is a slightly flattened globe, crunchy similar to an apple. Thus neither of the mentioned hybrids result in the characteristics of the present hybrid tomato as described herein.

This invention relates to a new paste-type hybrid tomato that is distinguished from both of its parents. This new hybrid tomato plant, cultivar 'Esas' (named Tulip Tomato®, trademark of Applicant) is also distinguished from other tomato varieties of which Applicant is aware by virtues of several characteristics described herein, especially by its shape and hardy skin.

BRIEF DESCRIPTION OF THE DRAWINGS

The accompanying photographs show a number of specimens of the hybrid plant and its fruit throughout various stages of growth as experienced in the summer of 2010 in central Michigan. The plants were only watered by natural rainfall for the entire growing season.

DETAILED BOTANICAL DESCRIPTION OF THE PLANT

Figure 3:
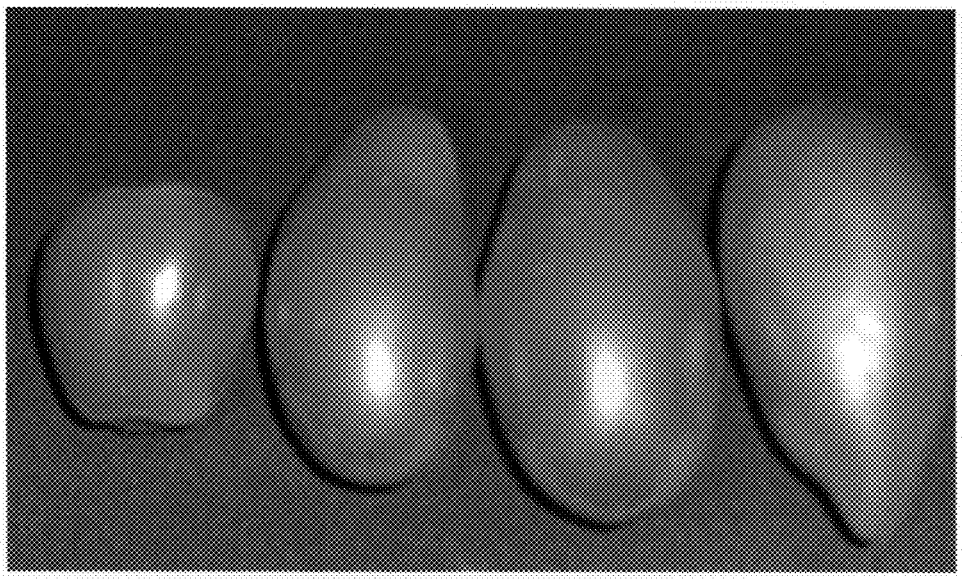
FIG. 3 is a photograph—from left to right—hybrid tomato 'Esas', Roma tomato, Roma tomato, and Amish tomato.

A detailed description of my new hybrid tomato is as follows—based upon my observation made from plants grown for about seven years in Michigan. The following outline sets forth a number of distinguishing features of this hybrid tomato over plants known before as seen in the photographs of the plant as attached hereto. The color specifications mentioned herein were determined by the reference to Federal Color Standard 595 revision B (FED-STD-595B). Some of these plant characteristics are as follows:

*Type.*—Paste — type tomato of indeterminate habit bearing a unique shaped fruit having 1-4 lobes with seed cavities corresponding to the number of lobes and a hardy skin. The 1 pointed lobe has 4 divisions and can be seen on the surface of the tomato, and has 4 seed cavities. The 2-4 lobes of the fruit are distinctive like a pepper (FIG. 3 shows 3 lobes). The seeds are distributed as usual in a tomato and not as found in a pepper.

*Breeding.*—Developed initially to Applicant's best knowledge and belief by accidental cross-breeding by a bee of an Amish tomato (seed parent) and Big Bertha Pepper (pollen parent) varieties and found in a cultivated area, and thereafter by deliberate selecting the most desirable characteristics of the next generation plants. The resulting plant holds its distinguishing characteristics through succeeding propagations by cuttings of the plant (such as taking the stem without roots and directly planting in soil without any pretreatment). This hybrid also has viable seeds so both asexual and sexual reproduction methods have been used by Applicant. Both methods yield the same hybrid fruit and display its characteristics.

*Seed parent.*—Amish tomato plant (*Solanum lycopersicum*) to Applicant's best knowledge and belief.

*Pollen parent.*—Big Bertha Pepper plant (*Capsicum anuum*) to Applicant's best knowledge and belief.

*Cultivar name.*—'Esas'.

*Propagation.*—Selection was made from the initial found plants in a cultivated area that were grown out both sexually from their seeds, asexually from cuttings of their stems, and a combination of seeds and cuttings. Further selections of plants over seven years were made based on shape and hardy skin. The present hybrid plant is a selection taken from the plants grown from seeds of the last generation and/or cuttings of the plants by taking stems and planting them. The seed plants and the cuttings plants produce the same fruit having the 1 to 4 lobes and the hardy skin. Both seeds and cuttings (if kept in an environment above freezing during winter) can be used to plant the hybrid plant the next growing season.

Plant:

*Habit.*—Indeterminate in growth habit, is hardy and may be used as a ground or staked variety. The stalk is thinner as compared to an Amish tomato. The foliage is relative sparse and about the same color (FS 34110) as the Amish tomato but the green (FS 34110) of the foliage is lighter than the Big Bertha Pepper. The plant reaches maturity in 75 to 90 days after transplanting depending on seasonal conditions. The fruit remains on the vine after being ripe for long periods of time (similar to a green pepper). This enables later picking of the ripe fruit to market as it does not readily fall to the ground soon after being ripe as do other tomato varieties.

*Growth.*—Medium size plant around 5 feet with an average rate of growth. The plants begin to blossom early in the season as the ground warms. Individual blossoms of this hybrid plant are five petal and star shaped.

Foliage: The plants are vine like and can be staked or not. There are numerous branches. The branches coming off the main stalk are close to the ground, and are about 1 to 4 inches apart. Additional leaf stalks and nodes grow on the branches.

Figure 1:
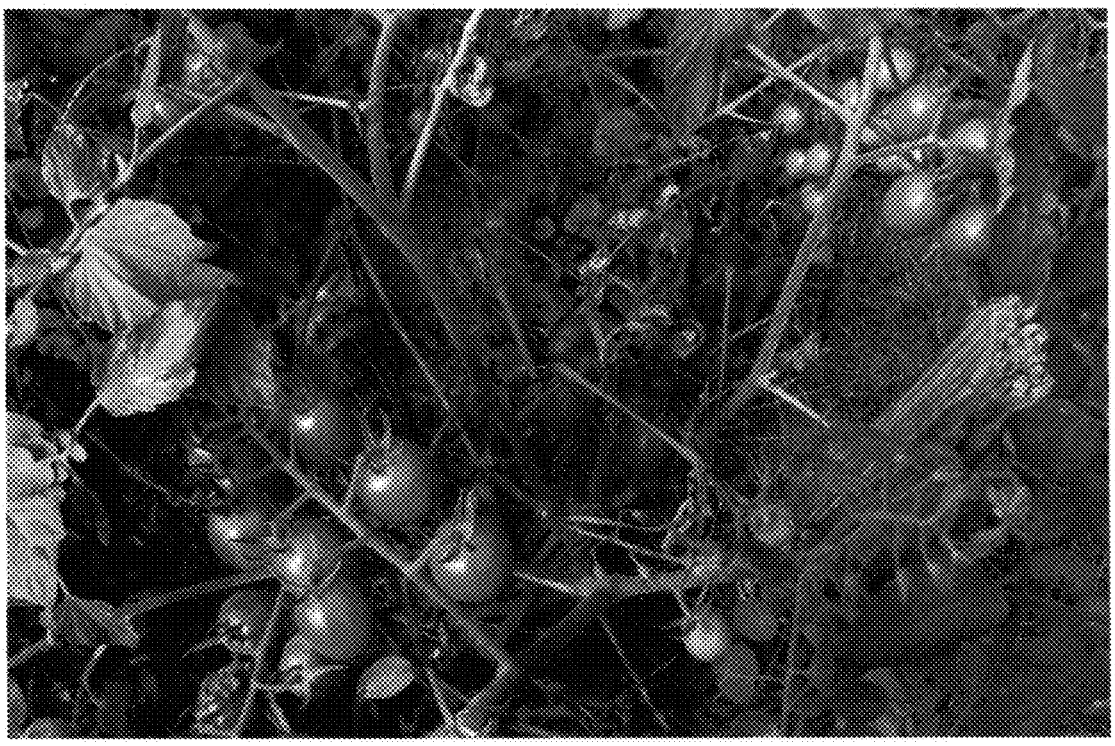
FIG. 1 is a photograph of the present hybrid tomato 'Esas' as growing on the vine and showing the clustering of the tomatoes as they grow.

*Size of leaf.*—(Mature) Leaves are 6 to 7 cm×4 cm and look the same as the Amish tomato variety. The leaf is elliptic in shape with margin teeth. The leaf type appears to be compound, odd pinnate. The surface texture for the upper surface is canaliculated (channeled) and the lower surface is pubescent (hairy). The leaves are shown in FIG. 1.

*Color.*—The upper leaf and the lower leaf is medium green (FS 34110).

*Main stems.*—132 to 137 cm long. (Tall); Color of the stem can vary with time of season and location, generally the color is brown (FS 34097); the surface texture is pubescent (hairy).

*Branches.*—8 to 10 branches from the main stem.

*New shoots.*—Up to 22, but new shoots will appear until frost.

*Flowers.*—The flowers begin from 4 to 6 weeks after planting and continue to form and flower until frost. There are 5, 6 or 7 petals for the flower; trumpet shaped; light yellow (in a range from FS 33481 to FS 33591); less than 1 inch in length. The outer most whorl consists of the sepals; collectively the sepals are the calyx. The sepal diameter is between ¾ to 1 inch, depending on maturity, surface texture is pubescent (hairy) color is green (FS 34097). Applicant has observed a 5 leaf sepal, 5 petal flower and a 6 leaf sepal, 6 petal flower on the same inflorescence this season. There is 1 gynoecium which is light green in color (FS 33814) having a width about 1/16 inch. The stigma extends out beyond the tip of the stamens. Syncarpous fruits develop from a single gynoecium having 2 to 4 carpels fused together as this hybrid has 2, 3 and 4 cavities. There are 2, 3 or 4 carpels per flower, color (FS 34097). The number of carpels in the flower corresponds to the number of locules from 2-4 found in the fruit. Androecium number 5, 6 or 7 stamens which correspond to the 5, 6 or 7 flower petals, respectively. Petiole size is less than an inch, surface texture pubescent (hairy) and color is green (FS 34097). Peduncle average size 2 to 5 cm, surface texture pubescent (hairy) and color is green (FS 34097). The amount of fruit born on the inflorescence depends on weather conditions. A total of 6, either fruits and/or flowers, have been observed on a 5 inch stem this season that is not over; previous seasons up to 13 fruit have been observed on an inflorescence and the stem grows longer to accommodate this increase. The present hybrid tomato stem is color (FS 34097) and branch color (FS 34097).

Fruit:

*Fruit.*—About 100 to 196 fruit from one plant is obtained in a season until frost. The fruit grows as clusters (inflorescence) of about 7 to 13 fruits on a branch, similar to cherry tomatoes. FIG. 1 illustrates this property.

Figure 2:
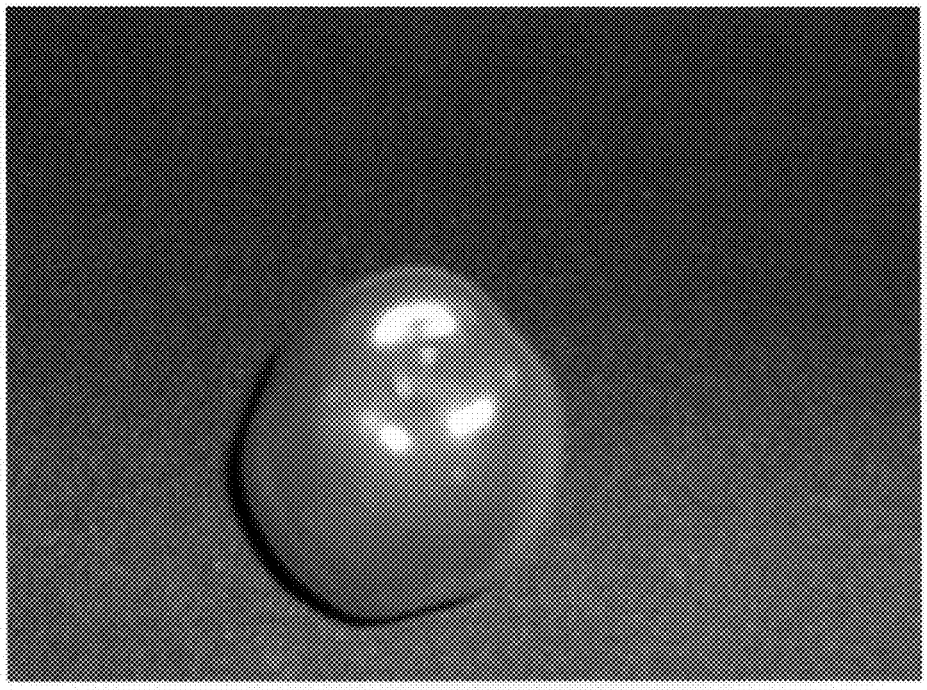
FIG. 2 is a photograph of a 3 lobe hybrid tomato 'Esas'.

*Shape.*—Similar to a green pepper or apple shape having 2 to 4 lobes all having definite division of sections similar to a green pepper. The lobes can be observed on the outside of the tomato and has internal seed cavities corresponding to the number of lobes, except the pointed or 1 lobe variety which has 4 seed cavities. FIG. 2 shows a 3 lobe hybrid tomato 'Esas'.

Figure 4:
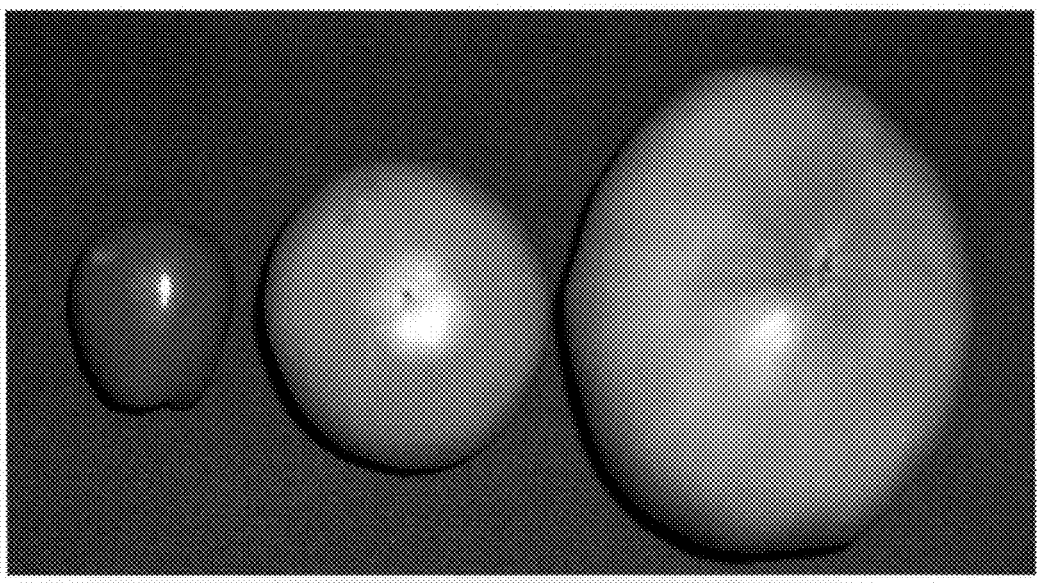
FIG. 4 is a photograph—from left to right—hybrid tomato 'Esas', Golden Girl tomato, and Mr. Stripey tomato.
Figure 5:
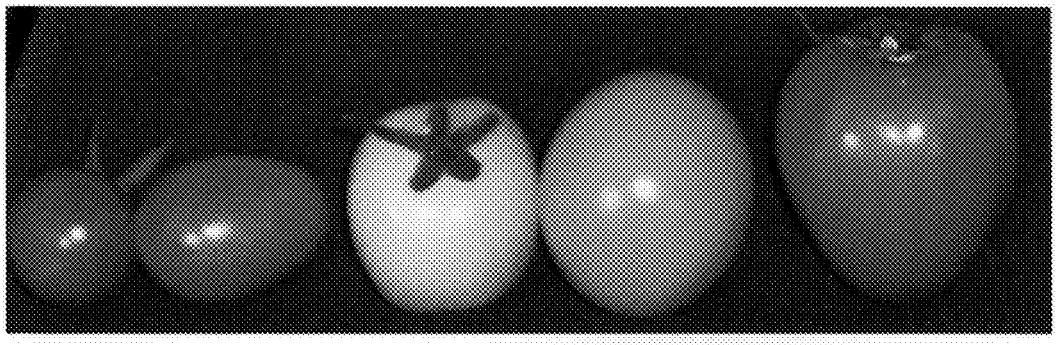
FIG. 5 is a photograph—from left to right—Cherry tomato, Grape tomato, Italian Ice, large yellow grape tomato, and hybrid tomato 'Esas'.

*Size.*—Average weight is about 15.75 to 27.45 grams, about 3.2 to 4 cm in width, and 3.7 to 4 cm in height. Thus this hybrid tomato 'Esas' is larger than a cherry tomato but smaller than its Amish tomato parent. See FIGS. 3, 4 and 5 showing these size differences. The core is an average 6.35 mm; wall is an average of 4.15 mm.

*Texture.*—Firm. The skin is hardy like a green pepper and the number of lobes represents the number of seed cavities, except the pointed or 1 lobe variety which has 4 seed cavities. The skin does not blanch off or separate when pressure cooked but rather disintegrates.

*Color (skin).*—Immature — light green (FS 33814) face with waxy appearance and often with a darker green (FS 34109) shoulder. Mature — light red (FS 33120) to red (FS 31128).

*Color (flesh).*—Light red (FS 33120) to red (FS 31128).

*Bearing season.*—The bearing season is from 75 to 90 days after transplanting or planting, and the plant will hold most fruit until frost (if the weather cooperates).

*Flavor.*—Mild tomato taste/meaty with low acid.

*Skin.*—The skin is quite tough, and similar to a green pepper.

*Seed.*—The seeds are present throughout the cavities of the fruit with an average of 81 seeds per fruit; on average a seed is 1/16 to 1/8 inch in a pear shape with a white color (FS 33532).

Figure 6:
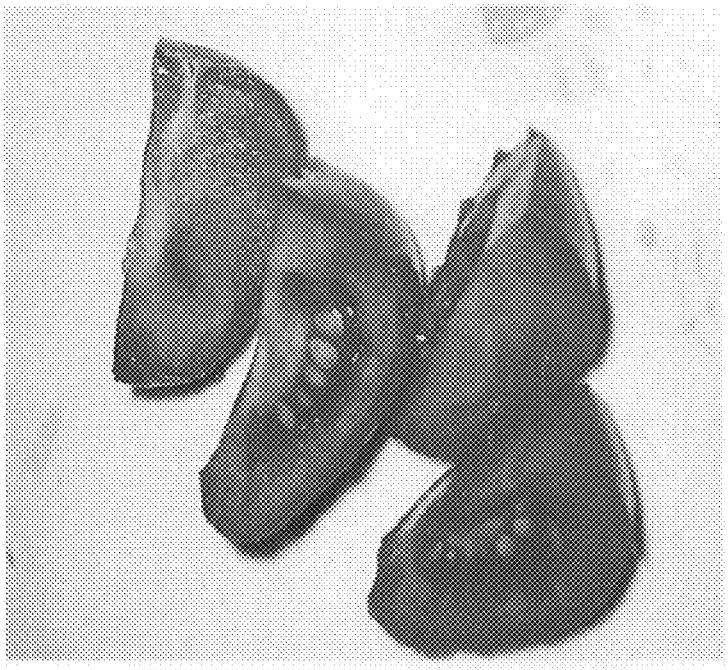
FIG. 6 is a photograph of a hybrid tomato 'Esas' cut open about 60 days after being picked and showing that it is still firm inside, with no visible deterioration but some wrinkling on the outer skin.

*Disease resistance.*—Similar to the Amish tomato resistance to fusarium wilts and verticillum — with the only insects seen being the tomato cut worm and grasshoppers. Fruit flies only happen if the fruit is damaged. If the fruit is not damaged, this hybrid resists rotting very well for long periods of time and the usual white fungus does not appear (disease resistant to fusarium wilt and verticillum). After picking a ripe fruit, the fruit will shrink inside itself over time, like the pepper, but can still be safely eaten months after picking. FIG. 6 shows a hybrid tomato 'Esas' after about 60 days from picking having these stated characteristics. (Note: Applicant has taken the seeds out of the tomato after 8 months and eaten the pulp. Taste is about the same as the usual fruit at picking.) Not all present hybrid tomatoes will last this long, but frequently do last on an average about 30 days to 8 months.

*Use.*—As a paste — type tomato for human consumption with likely ease of mechanical picking as it remains on the vine after ripening until frost.

*Bearing qualities.*—Quality: The plants have been grown for the last 9 years with the above qualities appearing every season and are shown fixed in the asexual reproduction of the plant.

Characteristics:

Applicant believes that these plants are hybrid tomatoes because of their very different characteristics from its parent tomato or pepper as follows:

5 petals for its flower (like a pepper);

the "skin" does not blanch off or separate when cooked in a pressure cooker but rather disintegrates without any skin pieces (unlike a tomato);

it has lobes (like a pepper), average 3-4 lobes but from 1-4 lobes are possible, with seeds in each lobe; when only 1 lobe is present, it has 4 compartments of seeds;

its size is larger than a cherry tomato and smaller than a Roma tomato or Amish tomato;

the tomatoes remain on the vine until frost or they are removed (like a pepper) as they do not fall from the vine when ripe (as do most tomatoes);

they can be picked until frost so fresh fruit is available all season;

if not bruised they do not rot (disease resistant to fusarium wilt and verticillum) after being picked (as do most tomatoes);

if not damaged can be kept in the open room temperature for 1 to 8 months and retain their flavor although they shrivel and loose size, like a pepper; and their outer skin is hardy and firm (like a pepper).

I claim:

1. A new and distinct variety of a hybrid tomato plant (*Solanum lycopersicum*×*Capsicum anuum* 'Esas') asexually prorogated substantially as herein described and illustrated.

* * * * *